(12) United States Patent
Aufseeser

(10) Patent No.: US 7,879,798 B1
(45) Date of Patent: Feb. 1, 2011

(54) COMPOSITION FOR INDOLENT WOUND HEALING AND METHODS OF USE THEREFOR

(75) Inventor: Leslie S. Aufseeser, Lakewood, NJ (US)

(73) Assignee: Regenicel, Inc., Lakewood, NJ (US)

( * ) Notice: Subject to any disclaimer, the term of this patent is extended or adjusted under 35 U.S.C. 154(b) by 594 days.

(21) Appl. No.: 11/895,474

(22) Filed: Aug. 24, 2007

(51) Int. Cl.
*A61K 38/12* (2006.01)

(52) U.S. Cl. ............... 514/2.3; 514/21.1; 530/319; 530/320

(58) Field of Classification Search ............ None
See application file for complete search history.

(56) References Cited

U.S. PATENT DOCUMENTS

| | | | |
|---|---|---|---|
| 3,622,668 A | 11/1971 | Moss et al. | |
| 4,223,018 A | 9/1980 | Belle | |
| 4,847,083 A * | 7/1989 | Clark | 424/642 |
| 5,061,689 A | 10/1991 | Alvarez | |
| 5,254,538 A | 10/1993 | Holick et al. | |
| 5,407,670 A * | 4/1995 | Shinault | 424/78.06 |
| 5,593,682 A | 1/1997 | Papas et al. | |
| 5,834,008 A | 11/1998 | Greenspan et al. | |
| 6,329,343 B1 | 12/2001 | Leung et al. | |
| 6,479,058 B1 * | 11/2002 | McCadden | 424/401 |
| 6,660,306 B2 | 12/2003 | Peshoff | |
| 7,094,431 B2 | 8/2006 | Peshoff | |
| 7,148,194 B2 | 12/2006 | Malik et al. | |

OTHER PUBLICATIONS

Simon, Harvey, "Periodontal Disease", http://www.mghadam.org/, Massachusetts General Hospital, Nov. 10, 2006.
American Diabetes Association, "Consensus Development Conference [Report] on Diabetic Foot Wound Care," Diabetes Care, vol. 22, pp. 1354-1360, Aug. 1999.
Dire, D.J. et al. "Prospective evaluation of topical antibiotics for preventing infections in uncomplicated soft-tissue wounds repaired in the ED." Academic Emergency Medicine, 2: 4-10, Jan. 1995.
Morley, J.E. et al. "Nutritional issues in nursing home care." Annals of Internal Medicine (USA). 123-11: 850-859, 1995.
Mazzotta, M.Y. "Nutrition and Wound Healing." J. Am. Podiatr. Med. Assoc. 84(9): 456-462, Sep. 1994.
Niedermeier, S. "Tierexperimentelle Untersuchungen zur Frage der Behandlung von Hornhautlasionen [Animal experiment studies on the problem of treating corneal lesions]." Klin. Monatsbl. Augenheilkd (Germany, West), 190 (1):28-9, Jan. 1987.
Seifter, E. et al. "Impaired Wound Healing in Streptozotocin diabetes. Prevention by supplemental Vitamin A." Ann. Surgery (US). 194(1): 42 -50, Jul. 1981.
Gilmore, O.J.A. et al. "Aetiology and prevention of wound infection in appendicetomy." British Journal [of] Surgery, 61:281-287, Mar. 1974.
Lowenfels, Albert B. "Viewpoints: Wound Healing With No Ointment, Non-antibiotic Ointment, or Antibiotic Ointment". Medscape General Surgery. 8(2), 2006.
United States Food and Drug Administration. "First Aid Antibiotic Drug Products", Code of Federal Regulations, Title 21, vol. 5, Chapter I, Part 333, Subpart B, pp. 222-225, Apr. 1, 2006.
Akpek, EK et al. "A randomized trial of low-dose, topical mitomycin-C in the treatment of severe vernal keratoconjunctivitis." Ophthalmology, 107(2):263-9. Feb. 2000.
Katz, Edward and Demain, Arnold L. "The Peptide Antibiotics of Bacillus: Chemistry, Biogenesis, and Possible Functions." Bacteriological Reviews, vol. 41, No. 2, pp. 449-474, Jun. 1977.
Armstrong, David G., D.P.M and Lavery, Lawrence A., D.P.M., M.P. H., "Diabetic Foot Ulcers: Prevention, Diagnosis and Classification" American Academy of Family Physicians, www.aafp.org/afp/980315ap/armstron.html, pp. 1-7, Mar. 1998.
Brown, Jr., Clarence William, MD, "Complications of Dermatologic Laser Surgery" http://emedicine.medscape.com/article/1120837, pp. 1-5, Oct. 2009.

* cited by examiner

*Primary Examiner*—Christina Bradley
(74) *Attorney, Agent, or Firm*—Siegmar Silber, Esq.

(57) ABSTRACT

A topical ointment is described for use in the treatment of indolent wounds composed of fat-soluble vitamins, namely, vitamin A, vitamin D, vitamin E, and a subantimicrobial amount of polypeptide antibiotic, which, in turn, acts as a proteinase inhibitor. The active ingredients are combined with a pharmaceutically acceptable topical carrier of lanolin, white petrolatum, mineral oil, and admixtures thereof. In treating these difficult to heal wounds, the selection of the level of the antibiotic at near trace amounts was surprisingly found to be above the proteinase inhibiting threshold and below the wound irritation level. The formulation hereof produced unexpected healing results not found in vitamin-enriched ointments or in antibiotic ointments.

12 Claims, No Drawings

COMPOSITION FOR INDOLENT WOUND HEALING AND METHODS OF USE THEREFOR

BACKGROUND OF THE INVENTION

1. Field of the Invention

This invention is in the field of topical formulations for wound healing. In particular, the present invention relates to a novel composition for accelerating wound and ulcer healing. The topical formulation described herein is especially useful in the treatment of ulcers of diabetic patients.

2. Background Information

Indolent wounds, where healing either completely fails to take place or starts and subsequently fails to progress, present major problems. This particularly applies in elderly patients and in healing of wounds adjacent bony prominences.

A patient population for which wound healing is particularly difficult involves those with Type I or Type II diabetes. Progression of the diabetic state usually results in diminished circulation and a concomitant lessening of the blood supply to the extremities of the body. Thus, wounds among the diabetic population, particularly those wounds that are sustained on the feet or legs, suffer from a lack of the circulating nutrients necessary for the wound healing to occur.

The wound healing process has been the subject of much study. In order to discuss wounds a classification is necessary. While wounds are classified using different systems, the traditional system is the Wagner classification system. Wagner classifies wounds by their depth and also whether or not the site is infected. Medical procedures include progressive monitoring of wound condition using the original classification and measurement.

The role of antibiotics in wound healing is of interest. When infection is present in the wound, antibiotics are necessary to overcome the infection even though at therapeutically effective levels antibiotics irritate the wound site. While the mechanism of wound healing is not fully understood, it is known that certain polypeptides and antibiotics, especially polypeptide antibiotics, inhibit proteinases, particularly healing-disruptive matrix metalloproteinases (MMP's). As will become apparent from the description that follows, the use of even subantimicrobial levels of antibiotics have been found to irritate wounds and interfere with the healing process.

According to *Wound Healing; an Overview of Acute, Fibrotic and Delayed Healing by* Diegelmann et al. (Frontiers in Bioscience 9, 283-239, Jan. 1, 2004), acute wounds normally heal in a very orderly and efficient manner characterized by four distinct, but overlapping phases: hemostasis, inflammation, proliferation and remodeling. Specific biological markers characterize healing of acute wounds. Likewise, unique biologic markers also characterize pathologic responses resulting in fibrosis and chronic non-healing ulcers.

Diegelmann et al. further indicate that the normal healing response begins the moment the tissue is injured. As the blood components spill into the site of injury, the platelets come into contact with exposed collagen and other elements of the extracellular matrix. This contact triggers the platelets to release clotting factors as well as essential growth factors and cytokines such as platelet-derived growth factor (PDGF) and transforming growth factor beta (TGF-B). Following hemostasis, the neutrophils then enter the wound site and begin the critical task of phagocytosis to remove foreign materials, bacteria and damaged tissue. As part of this inflammatory phase, the macrophages appear and continue the process of phagocytosis as well as releasing more PDGF and TGFB.

Once the wound site is cleaned, fibroblasts migrate in to begin the proliferative phase and deposit new extracellular matrix. The new collagen matrix then becomes cross-linked and organized during the final remodeling phase. In order for this efficient and highly controlled repair process to take place, there are numerous cell-signaling events that are required.

In indolent wounds such as non-healing ulcers, this efficient and orderly process that Diegelmann et al. describe is lost and the ulcers are locked into a state of chronic inflammation, characterized by abundant neutrophil infiltration with associated reactive oxygen species and destructive enzymes. Healing proceeds only after the inflammation is controlled. Thus it is believed that wounds and ulcers that do not heal contain an excessive amount of neutrophils. The neutrophils, in turn, produce metalloproteinases (MMP's). MMP's break down the extracellular matrix (ECM), which connects cells together to form tissue. If MMP's dominate, the tissue necessary to repair the wound will not form. The body has some natural MMP inhibitors tissue inhibitors of metalloproteinases (TIMP's). Supplementation with added MMP inhibitors ensures sufficient inhibition for wound healing. For the typical formulation taught herein, subantimicrobial amounts of polypeptide antibiotics serve as proteinase inhibitors.

In the literature, subantimicrobial amounts of non-polypeptide antibiotics are also described a MMP inhibitors. An example of this is noted in November 2006 *Periodontal Disease* review by Harvey Simon, MD, Associate Professor of Medicine, Harvard Medical School; Physician, Massachusetts General Hospital, wherein doxycycline is an MMP inhibitor. There have also been polypeptide chains that have inhibited MMP's. U.S. Pat. No. 7,148,194 describes that these polypeptide chains called proenzyme leader sequences impact healing by re-forming MMP's to their undifferentiated, proenzyme state and thereby inhibiting the destructive enzymatic activity.

The healing mechanism and the effect of polypeptide antibiotics on wound healing are not fully understood. As taught by the inventor hereof, near trace amounts of polypeptide antibiotics work to heal wounds, while higher amounts of polypeptide antibiotics (still in the subantimicrobial range) irritate the wound and prevent healing.

Vitamin D and its analogs have been mentioned in the prior art as suitable therapeutics for the treatment of indolent wounds, especially for the healing of decubitus or diabetic ulcers of the feet. Of note in connection to this is U.S. Pat. No. 5,254,538 to Holick et al. entitled Method of Treating Periodontal Disease, which is hereby incorporated by reference in its entirety. Also noted are the references cited therein. However, there still exists a need for a specific therapy for the healing of wounds which are resistant to standard therapeutic agents. Accordingly, the present invention is directed to these ends.

SUMMARY

This patent pertains to a topical ointment to be used in the treatment of indolent wounds composed of fat-soluble vitamins—vitamin A, vitamin D, vitamin E—and a subantimicrobial amount of proteinase inhibitor, in a pharmaceutically acceptable topical carrier. Examples of acceptable carriers are lanolin, white petrolatum, mineral oil, and admixtures thereof. In non-infected indolent wounds, ointments with therapeutically recommended levels of antibiotics have been known to irritate wound sites and retard healing. Surprisingly, near trace amounts of some antibiotics, significantly below the antimicrobial level, have been found to help the healing process.

The proteinase inhibitor is a near trace amount of polypeptide antibiotic. A specific example of the polypeptide antibiotic component is a combination of bacitracin and polymyxin B sulfate. The antibiotic is present in an amount that is sufficiently limited so as not to cause irritation, but sufficient to inhibit destructive, healing-retarding proteinases that the body produces in excess during a pathologic wound healing process. While the wound healing process is not fully understood, bringing the combination of the vitamin enriched ointment and proteinase inhibition to the wound site has produced surprising and unexpected results not found otherwise in vitamin enriched ointments or in antibiotic ointments.

OBJECTS AND FEATURES OF THE INVENTION

It is thus an object of the present invention to provide a novel therapeutic composition for the treatment of wounds.

It is a further object of the present invention to provide a composition to heal wounds which have been classed as indolent wounds and are generally recalcitrant to standard, wound healing therapies.

It is a still further object of the present invention to provide, using the composition of this invention, for the healing f ulcers such as decubitus, diabetic ulcers, venous ulcers, arterial ulcers, traumatic ulcers, peripheral vascular disease ulcers, and gouty ulcers.

It is yet another object of the present invention to provide using the composition of this invention, for the healing of wounds in diabetic or other similar patients having impaired circulation, using the composition of the invention.

It is a still yet further object of the present invention to provide a composition for the first aid, especially to diabetic patients and patients with poor circulation that is superior to standard first aid products.

It is thus a feature of the present invention to provide a novel therapeutic composition wherein the antibiotic ingredient is at a nonirritating level.

It is a further feature of the present invention to provide a novel therapeutic composition wherein the polypeptide antibiotic is present in a sufficient amount to inhibit the formation of destructive proteinases.

Other objects and features of the present invention will become apparent upon reading the Description and Claims which follow.

DESCRIPTION OF THE PREFERRED EMBODIMENT

In this description of the topical ointment of this invention, the antibiotic component does not function in an antibacterial role. It has been found through many indolent wound cases that the polypeptide antibiotics are unusually proficient in inhibiting the development of MMP's and other destructive enzymes. Also, at levels well below the antimicrobial effectiveness, this class of antibiotics still irritates the wound. After treating many wound cases, the concentrations of polypeptide antibiotics has been adjusted to values below the wound-irritating range and above, what is believed, to be the destructive-enzyme-inhibiting threshold.

The topical ointment of this invention enhances cell regeneration at the wound site and is surprisingly non-irritating and anti-inflammatory. Additionally, the polypeptide antibiotic present in the lower reaches of the subantimicrobial range is significantly enzyme inhibiting. Identification of the zone in which cell regeneration occurs without irritation or inflammation, while suppressing destructive enzyme activity, is not found in the literature describing such topical ointment formulations. When the method of treating indolent wounds, as described herein, is employed healing occurs at optimal rates. By way of introduction a few terms are first defined.

In this application, the term subantimicrobial amount is defined as an amount of polypeptide antibiotic in at least an order of magnitude below the effective level for bactericidal and bacteriostatic activity. Thus, for a polypeptide antibiotic such as bacitracin, wherein an effective dose is 500 units/gram (14,000 units/oz), for purposes of this application, the subantimicrobial amount is below 100 units/gram (2,800 units/oz). For polymyxin B sulfate, wherein an effective antibacterial dose is 5,000 units/gram (140,000 units/oz), for purposes of this application, the subantimicrobial amount is below 1,000 units/gram (28,000 units/oz).

For the purposes of this application, a near trace amount is defined as an amount of polypeptide antibiotic that is less than 10% of the effective level for bacterial and bacteriostatic activity. Thus, for a polypeptide antibiotic such as bacitracin, wherein an effective dose is 500 units/gram (14,000 units/oz), for purposes of this application, the near trace amount is below 50 units/gram (1,400 units/oz). For polymyxin B sulfate, wherein an effective antibacterial dose is 5,000 units/gram (140,000 units/oz), for purposes of this application, the near trace amount is below 900 units/gram (25,200 units/oz).

The present invention provides a composition for healing wounds to the external epithelium, including cuts, punctures, and lacerations. The invention also provides for the treatment of ulcers, especially diabetic ulcers, decubitus ulcers, peripheral vascular disease ulcers, venous ulcers, arterial ulcers, pressure ulcers, traumatic ulcers, burns, wound dehiscence, skin abrasions, blisters, gouty ulcers, post-operative secondary intention healing, incisions and the like, especially in diabetic or other patients having impaired circulation.

The vitamin components of the composition of the present invention are each well-known and commercially available. All the vitamin components are fat-soluble and are readily solubilized in the topical carrier, infra, hereof. Numerous vitamin D derivatives equivalent to vitamin D itself are known in the art and these may also be utilized in place of the vitamin D. Typically, the vitamin A and K are supplied by cod liver oil. Similarly, the polymyxin B sulfate can be utilized as various other pharmacologically acceptable salts, although the polymyxin B sulfate is preferred since this is the commercially available salt.

Preferably, the final composition of the present invention will contain, 500 to 750 units/gram vitamin A, 35 to 75 units/gram vitamin D, 90 to 125 units/gram vitamin E, 20 to 50 units/gram bacitracin zinc, and 360 to 900 units/gram polymyxin B (as a salt).

More preferably, the formulation will contain about 600 units vitamin A, 60 units vitamin D, 115 units vitamin E, 45 units bacitracin zinc, and 885 units polymyxin B (as a salt) per gram of finished formulation.

The composition of the present invention is administered in an appropriate pharmaceutically acceptable carrier for topical administration. Particularly preferred are carriers typically utilized for wound healing, ulcer healing, and the inhibition of scar formation in animals, especially humans.

The composition is typically employed in an ointment dosage form adapted for topical use. Alternatively, the composition can be present in a pharmacologically inert topical carrier, such as one comprising a gel, or a cream, including such carriers as water, glycerol, alcohol, propylene glycol, fatty alcohols, triglyceride, fatty acid esters or mineral oils.

Other possible carriers include liquid petrolatum, paraffin, lanolin, isopropyl palmitate, and polyethylene glycol. The composition may also be utilized as part of a component of a patch for transdermal administration.

While a mixture of bacitracin zinc and polymyxin B (as a salt) has been used in the above formulation as a proteinase inhibitor, the polypeptide antibiotic component may be selected from the group consisting of bacitracin, polymyxin, cyclosporin, viomycin, colistin, gramicidin, tyrocidine, actinomycin, antimycin, lysostaphin, myxothiazol, nisin, paracelsin, echinomycin, valinomycin, hitachimycin and admixtures thereof.

The formulation of the present invention is readily prepared from a lanolin-, paraffin- and petrolatum-based ointment containing vitamin A and vitamin D supplied by an approximately 1% by weight cod liver oil admixture. This provides 850 USP units vitamin A per gram and 85 USP units vitamin D per gram. To this composition of vitamins A and D in lanolin, white petrolatum, and paraffin is added the desired amounts of vitamin E and the powdered polymyxin B sulfate-bacitracin zinc in a lactose carrier.

Formulating the composition in this manner results in a topical preparation having the desired consistency for application of the wound or ulcer under treatment and containing the active agents in the desired proportions, i.e., per gram of finished composition, approximately
- 600 units vitamin A;
- 60 units vitamin D;
- 115 units vitamin E;
- 885 units polymyxin B sulfate; and,
- 45 units bacitracin zinc.

This composition is prepared by mixing 16 ounces (454 grams) of the commercially available vitamin A and D ointment (containing 0.937% by weight cod liver oil), 60 ml of vitamin E oil (64,000 international units) with 50 grams of Polysporin® antibiotic powder (each gram containing 10,000 units polymyxin B sulfate and 500 units bacitracin zinc on a lactose base). The ingredients are mixed and ready for use.

The dosage of the composition of the present invention will be dependent upon the age, health, and weight of the patient under treatment, and as well as taking into consideration any other concurrent treatment. Typically, the composition of the present invention is applied 2 to 3 times per week. However, depending on the severity of the wound under treatment, one of ordinary skill in the art can determine the optimal dosage regimen. When used as a first aid ointment, it is applied daily.

What is claimed is:

1. A method of healing indolent wounds comprising topically contacting said wound with an ointment composition consisting of:
   - 500 to 750 units of vitamin A;
   - 35 to 75 units vitamin D;
   - 90 to 125 units vitamin E;
   - and a proteinase inhibitor being a nonirritating admixture of a near trace amount of bacitracin zinc and a near trace amount of polymyxin B sulfate,
   - in a pharmaceutically acceptable topical carrier selected from a group consisting of lanolin, white petrolatum, mineral oil, and admixtures thereof.

2. A method of healing indolent wounds comprising topically contacting said wound with an ointment composition consisting of:
   - 500 to 750 units of vitamin A;
   - 35 to 75 units vitamin D;
   - 90 to 125 units vitamin E;
   - and a proteinase inhibitor being a nonirritating admixture of bacitracin zinc present in an amount of below 50 units per gram and polymyxin B sulfate present in an amount of below 900 units per gram,
   - in a pharmaceutically acceptable topical carrier selected from a group consisting of lanolin, white petrolatum, mineral oil, and admixtures thereof.

3. The method of claim 1, wherein said bacitracin zinc is present in the amount of 45 units per gram.

4. The method of claim 1, wherein said polymyxin B sulfate is present in the amount of 885 units per gram.

5. The method of claim 1, wherein said bacitracin zinc is present in the amount of 45 units per gram, and said polymyxin B sulfate is present in the amount of 885 units per gram.

6. A method of healing diabetic ulcers comprising topically contacting said wound with an ointment composition consisting of:
   - 500 to 750 units of vitamin A;
   - 35 to 75 units vitamin D; 90 to
   - 125 units vitamin E;
   - and a proteinase inhibitor being a nonirritating admixture of a near trace amount of bacitracin zinc and a near trace amount of polymyxin B sulfate,
   - in a pharmaceutically acceptable topical carrier selected from a group consisting of lanolin, white petrolatum, mineral oil, and admixtures thereof.

7. The method of claim 6, wherein said bacitracin zinc is present in the amount of 45 units per gram.

8. The method of claim 6, wherein said polymyxin B sulfate is present in the amount of 885 units per gram.

9. The method of claim 6, wherein said bacitracin zinc is present in the amount of 45 units per gram, and said polymyxin B sulfate is present in the amount of 885 units per gram.

10. The method of claim 2, wherein said bacitracin zinc is present in the amount of 45 units per gram.

11. The method of claim 2, wherein said polymyxin B sulfate is present in the amount of 885 units per gram.

12. The method of claim 2, wherein said bacitracin zinc is present in the amount of 45 units per gram, and said polymyxin B sulfate is present in the amount of 885 units per gram.

* * * * *